(12) United States Patent
Altrogge et al.

(10) Patent No.: US 9,249,384 B2
(45) Date of Patent: Feb. 2, 2016

(54) METHOD AND DEVICE FOR THE ELECTRICAL TREATMENT OF REACTION SPACES

(75) Inventors: Ludger Altrogge, Mechernich (DE); Timo Gleissner, Euskirchen (DE); Andreas Heinze, Köln (DE); Herbert Müller-Hartmann, Köln (DE); Andreas Wirth, Weidenberg (DE)

(73) Assignee: LONZA COLOGNE GMBH, Cologne (DE)

( * ) Notice: Subject to any disclaimer, the term of this patent is extended or adjusted under 35 U.S.C. 154(b) by 1007 days.

(21) Appl. No.: 13/145,113

(22) PCT Filed: Jan. 20, 2010

(86) PCT No.: PCT/EP2010/000295
§ 371 (c)(1),
(2), (4) Date: Nov. 30, 2011

(87) PCT Pub. No.: WO2010/083985
PCT Pub. Date: Jul. 29, 2010

(65) Prior Publication Data
US 2012/0077245 A1    Mar. 29, 2012

Related U.S. Application Data

(60) Provisional application No. 61/146,250, filed on Jan. 21, 2009.

(30) Foreign Application Priority Data

Jan. 20, 2009   (EP) ..................................... 09000698

(51) Int. Cl.
   *C12M 1/42*    (2006.01)
(52) U.S. Cl.
   CPC ..................................... *C12M 35/02* (2013.01)
(58) Field of Classification Search
   None
   See application file for complete search history.

(56) References Cited

U.S. PATENT DOCUMENTS

| | | |
|---|---|---|
| 6,010,613 A | 1/2000 | Walters et al. |
| 6,150,148 A | 11/2000 | Nanda et al. |
| 2004/0014220 A1 | 1/2004 | Siebenkotten et al. |
| 2004/0137603 A1 | 7/2004 | Muller-Hartmann et al. |
| 2004/0137622 A1 | 7/2004 | Schmidt et al. |
| 2006/0087522 A1 | 4/2006 | Muller-Hartmann et al. |
| 2008/0213854 A1 | 9/2008 | Wirth et al. |
| 2008/0220527 A1 | 9/2008 | Schmidt et al. |
| 2009/0023131 A1 | 1/2009 | Muller-Hartmann et al. |
| 2012/0067639 A1 | 3/2012 | Altrogge et al. |
| 2012/0087841 A1 | 4/2012 | Altrogge et al. |

FOREIGN PATENT DOCUMENTS

| | | |
|---|---|---|
| EP | 1 577 378 A1 | 9/2005 |
| EP | 1 961 807 A1 | 8/2008 |
| WO | 91/18103 A1 | 11/1991 |
| WO | 03/057819 A1 | 7/2003 |
| WO | 2008036800 A2 | 3/2008 |

*Primary Examiner* — Robert Yamasaki
(74) *Attorney, Agent, or Firm* — Joyce von Natzmer; Agris & von Natzmer LLP

(57) ABSTRACT

The invention relates to a method for applying at least one electrical voltage pulse to at least one reaction space by at least partially discharging at least one charge storing unit for storing electrical charges. According to the invention the method comprises applying at least one voltage pulse to a reaction space by at least partially discharging a second charge storing unit and simultaneously charging or partially discharging a first charge storing. Furthermore, the invention relates to a device 1 for applying at least one electrical voltage pulse to at least one reaction space, comprising at least two charge storing units (10, 11) for storing electrical charges and at least one power supply unit (12) for charging the charge storing units (10, 11) and/or at least one discharge device for partially discharging the charge storing units (10, 11). According to the invention it is provided that at least two of the charge storing units (10, 11) form a common storage module which can be discharged at any time.

4 Claims, 9 Drawing Sheets

Figure 1:
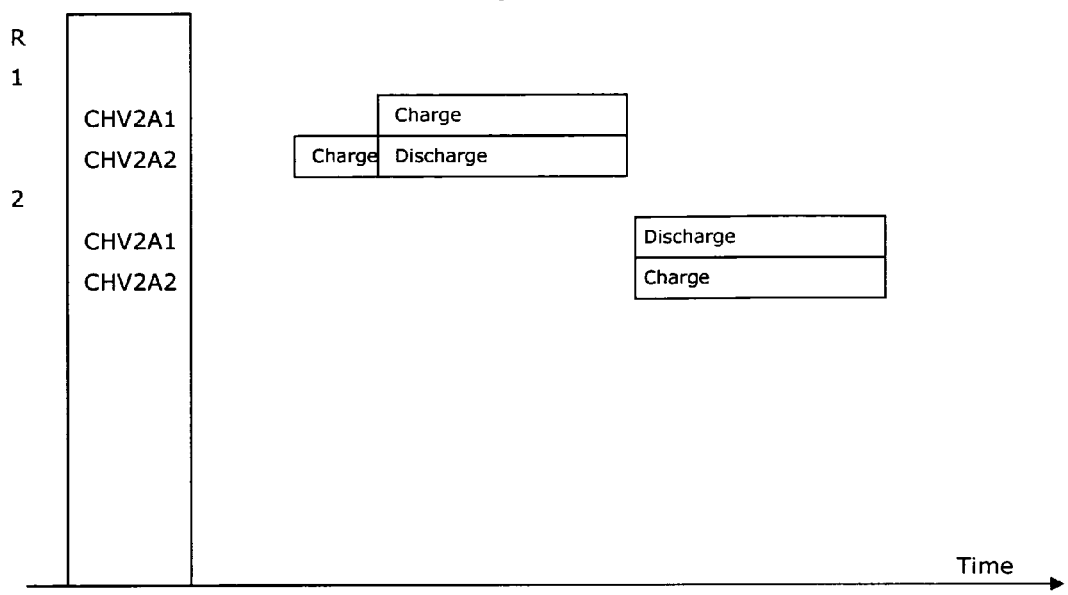

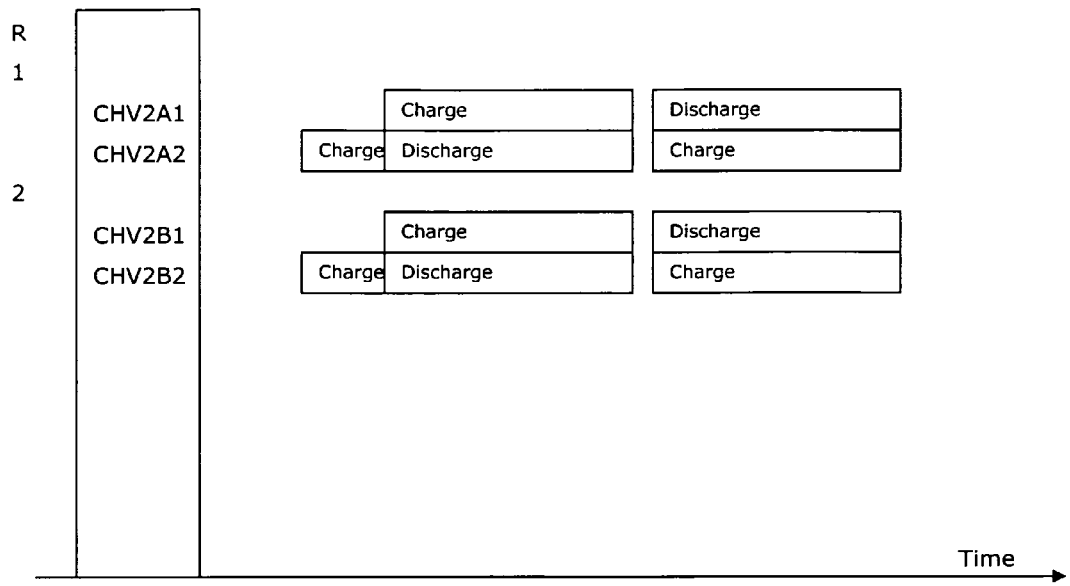
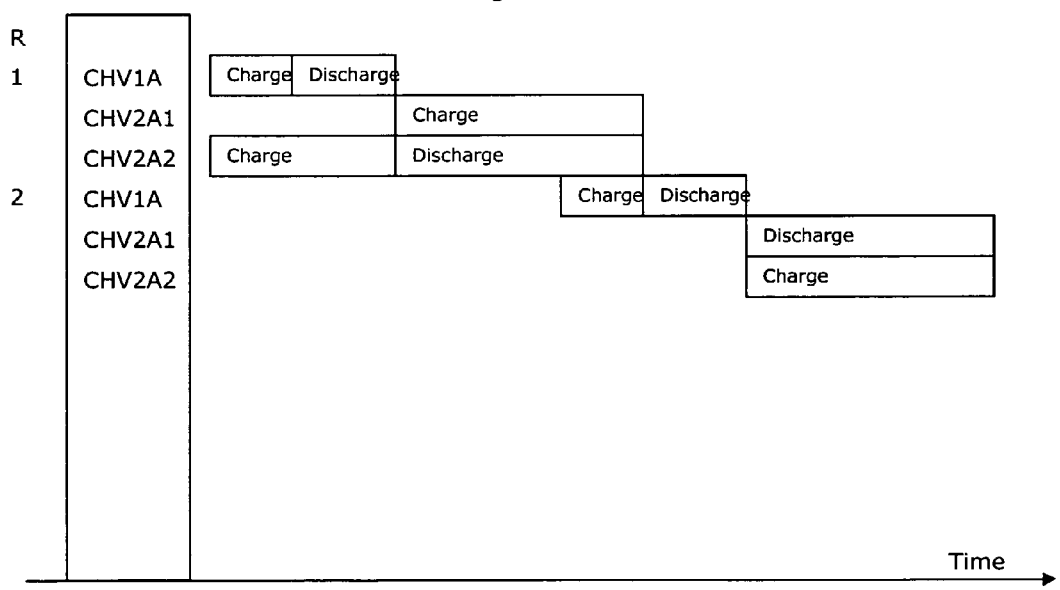

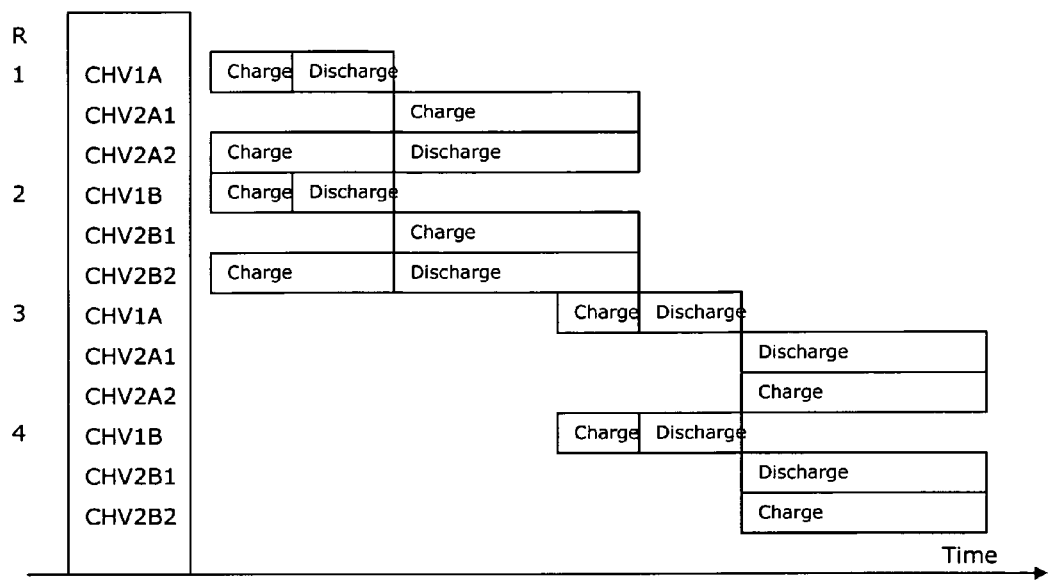
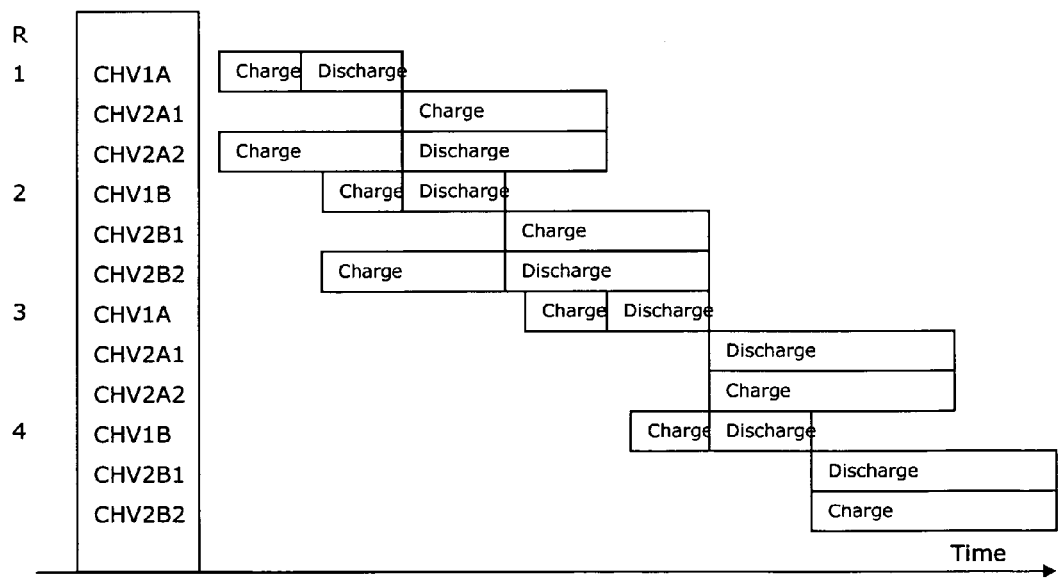

METHOD AND DEVICE FOR THE ELECTRICAL TREATMENT OF REACTION SPACES

This is the U.S. national stage of International application PCT/EP2010/000295, filed Jan. 20, 2010 designating the United States, claiming priority to European patent application no. EP 09000698.2, filed Jan. 20, 2009 and the benefit of U.S. provisional application No. 61/146,250, filed Jan. 21, 2009.

The invention relates to a method for applying at least one electrical voltage pulse to at least one reaction space by discharging at least one charge storing unit for storing electrical charges. The invention further relates to a device for applying at least one voltage pulse to at least one reaction space, which comprises at least two electrical charge storing units for storing electrical charges and at least one power supply unit for charging the charge storing units and/or at least one discharge device for partially discharging the charge storing units.

The introduction of biologically active molecules such as DNA, RNA or proteins into living cells represents an important instrument for examining biological functions of these molecules. A preferred method for introducing foreign molecules into the cells is electroporation, which in contrast to chemical methods is not reliant upon the simultaneous transport of other biologically active molecules. With electroporation the foreign molecules are introduced by a momentary current flow into the cells from a buffer solution adapted to the cells or a cell culture medium, whereby due to the effect of the electrical voltage pulse or the electrical field and current flow created thereby the cell membrane is made permeable for the foreign molecules. Frequently the cell suspension is housed in a so-called cuvette, i.e. a narrow open vessel, the specimen space of which comprises two opposing parallel electrodes in the lateral walls which are used to apply the electrical voltage. Due to the momentarily created "pores" in the cell membrane the biologically active molecules initially reach the cytoplasm in which, as applicable, they can perform their investigative function, and then also, given certain conditions, the core of the cell. Due to the momentary application of a strong electrical field, i.e. a momentary voltage pulse of high current density, it is additionally possible to fuse cells, cell derivatives, sub-cellular particles and/or vesicles. With this so-called electrofusion the cells are, for example, initially brought into close membrane contact by an inhomogeneous electrical alternating field. Subsequent application of an electrical field pulse results in parts of the membrane starting to interact which ultimately leads to the fusion. The devices used for electrofusion may be similar to the apparatuses used for electroporation. In addition living cells may also be stimulated by electrical fields in a way which changes their properties.

Receptacles with several reaction spaces for the electroporation, electrofusion or electrostimulation of living cells as well as all applications, where the starting solution must be exposed to an electrical field as well as to an electrical current, are used, above all, in bio-chemical and pharmaceutical applications, if a plurality of starting solutions has to be tested simultaneously. The aim is to make a maximum number of reaction spaces available in one receptacle, for example 96 or 384, in particular for HT analyses (HT=high throughput), since here a plurality of specimens is to be tested within the shortest possible time. Receptacles of this kind are, as a rule, multihole plates, microtiter plates or multiwells. Normally the receptacles consist of several reaction spaces each comprising two electrodes, which are in contact with the starting solution of, for example, a cell suspension inside the reaction space. The two electrodes of a reaction space create an electrical field when an electrical voltage is applied to the inside the reaction space. With electrically conducting substances, apart from the electrical field, an electrical current is created due to the surrounding electrodes of different polarity. The equal polarity electrodes, i.e. all cathodes and/or all anodes for example, of different reaction spaces are formed either in one piece or are electrically coupled to each other allowing them to be connected to the voltage source via a common electrical contact.

When electrically treating such microtiter plates one problem consists in the fact that the time required for applying one or several voltage pulses to individual reaction spaces is very long. The reason for this is that in particular when reaction vessels are processed individually, very many voltage pulses must be emitted in succession which makes very high demands upon the capacities and charging times of the charge storing units or capacitors used, in particular for high voltage values and/or energies of the electrical pulses.

Methods and devices for applying several electrical voltage pulses to reaction spaces are known. The U.S. Pat. No. 6,150,148, for example, discloses a method and a device for electroporation, whereby several voltage pulses are generated for admission to a reaction space. The device comprises a voltage source by means of which two capacitors can be charged via a voltage divider and one transistor, respectively. The capacitors are discharged via controllable switches so that several successive voltage pulses, for example at least one voltage pulse with a relatively high voltage amplitude and at least one voltage pulse with a lesser voltage amplitude, can be applied to the reaction space. When applying such sequences of voltage pulses to several reaction spaces in succession, however, this device is disadvantageous in that the two capacitors must be recharged after each treatment of a reaction space or at least after the treatment of just a very few reaction spaces, so that pauses occur again and again which altogether prolong the process time.

Furthermore the U.S. Pat. No. 6,010,613 discloses a method and a device for generating a sequence of voltage pulses. Here the voltage pulses are generated by the almost complete discharge of a single capacitor which has a capacity sufficient for generating one pulse sequence. In order to generate the next pulse or next pulse sequence the capacitor must first be recharged to the required voltage amplitude. The time required for this has a negative effect upon the total process duration when many reaction spaces are to be treated.

It is the object of the invention to provide a method and a device with which one or several voltage pulses, respectively, can be applied to reaction spaces within a minimum amount of time.

According to the invention this object is met by a method for applying at least one electrical voltage pulse to at least one reaction space by at least partially discharging at least one charge storing unit for storing electrical charges, which method comprises the following steps:

a) Applying at least one voltage pulse to at least one reaction space by at least partially discharging a first charge storing unit and simultaneously charging or partially discharging a second charge storing unit;

b) Applying at least one voltage pulse to the same reaction space or a further reaction space by at least partially discharging the second charge storing unit and simultaneously charging or partially discharging the first charge storing unit discharged during step a).

With the method according to the invention no time is lost for charging the charge storing unit between successive electrical treatments due to at least partially charging and discharging the first or second charge storing unit in parallel or simultaneously, resulting in the total process duration being distinctly reduced. Due to cyclically discharging one charge storing unit and simultaneously charging or partially discharging another charge storing unit at least one charged charge storing unit is always available for the next discharge operation, so that no additional time is required for charging or partially discharging a charge storing unit between two discharge operations, provided they last less long than the discharge operation. The method according to the invention therefore allows very rapid voltage pulse sequences to be performed, be it for applications with multiple pulses or for applications, where voltage pulses have to be applied successively and/or simultaneously to several reaction spaces. In particular in the case of high throughput processes the process duration can thereby be distinctly reduced.

"At least partially discharging" in terms of the invention means that the respective charge storing unit does not have to be completely discharged when emitting a voltage pulse, but that it merely emits the voltage difference which is required for the voltage pulse. That is, a residual voltage may remain in the charge storing unit after discharging.

"Simultaneous" in terms of the invention means that the charge and discharge operations run synchronously at least partially, i.e. the two operations may run either synchronously or may be staggered in terms of time, whereby in the latter case an operation is still or already running whilst the other operation has already finished or has not yet started. Since the at least partial discharge operation during emitting a voltage pulse may be a very short event in terms of time, the respective charge storing unit in this case will be inactive during the "simultaneous" charge or partial discharge operation prior to the start and/or after the end of the discharge operation, until the longer-lasting charge or partial discharge operation is completed.

"Charging or partial discharging" in terms of the invention means that the charge storing unit is made ready to emit the next or following voltage pulse. That means that the voltage level in the charge storing unit is adapted to match the voltage required for the next voltage pulse. This may be done, on the one hand, by charging the charge storing unit up to the voltage required for the next voltage pulse or, on the other hand, by partially discharging it down to the voltage envisaged for the next voltage pulse. In the second case the voltage level in the charge storing unit is adapted to match the new lower voltage level for the next reaction space by partially discharging it by means of a discharge device, for example an electrical load, preferably a discharge resistance.

It is especially advantageous if all steps up to completion of the process are repeated as often as liked and/or if the process is completed after the last step has been carried out. Preferably the method according to the invention is repeated several times, that is, several cycles of the process steps are performed which will allow, for example, a great many reaction spaces to be treated electrically in succession, whereby the process is not completed until at least one voltage pulse has been applied to all reaction spaces to be treated. The method according to the invention therefore can be employed, for example, without problems in high throughput processes using multiwell plates, preferably 96-well or 384-well plates.

In an advantageous development of the invention the method may comprise the following steps:
a) Applying at least one voltage pulse to at least two reaction spaces by at least partially discharging two first charge storing units and simultaneously charging or partially discharging two second charge storing units;
b) Applying at least one voltage pulse to the same reaction spaces or to a further two reaction spaces by at least partially discharging the two second charge storing units and simultaneously charging or partially discharging the two first charge storing units at least partially discharged during step a).

The method according to the invention can therefore be employed for applying several voltage pulses to a single reaction space or a cuvette or for electrically treating several reaction spaces. In the latter case voltage pulses may be applied in succession to many reaction spaces within a short time, whereby at least two reaction spaces can always be treated simultaneously. With the method according to the invention therefore voltage pulses can be simultaneously applied to at least two reaction spaces in an advantageous development of the invention, so that the speed of the treatment of several reaction spaces is distinctly increased.

In a further advantageous development of the invention the method may comprise the following steps:
a) Applying at least one voltage pulse to at least one reaction space by at least partially discharging a first charge storing unit;
b) Applying at least one further voltage pulse to the reaction space by at least partially discharging the second charge storing unit and simultaneously charging or partially discharging a further second charge storing unit as well as the first charge storing unit discharged during step a).
c) Applying at least one voltage pulse to another or the same reaction space by at least partially discharging the first charge storing unit at least partially discharged during step a) and recharged or partially discharged during step b);
d) Applying at least one further voltage pulse to the reaction space from step c) by at least partially discharging the further second charge storing unit charged or partially discharged during step b) and simultaneously charging or partially discharging the second charge storing unit at least partially discharged during step b) as well as the first charge storing unit at least partially discharged during step c).

This solution according to the invention is advantageous, in particular, in a case when voltage pulses are to be generated which are composed of a short voltage pulse with a relatively high voltage amplitude and/or relatively low energy and a longer voltage pulse with a lesser voltage amplitude and/or higher energy. Where such dual voltage pulses are to be applied successively to several reaction spaces within a relatively short time, for example when using multiwell plates in a high throughput process, the time gaps between treating individual reaction spaces would be relatively long when using a single capacitor for the longer voltage pulse, since the capacitor, after being discharged and then recharged or partially discharged, would first have to be adapted to match the voltage specified for the next voltage pulse and this would require larger amounts of electrical energy. With the method according to the invention, by contrast, one of the two charge storing units is always being discharged, whilst the other charge storing unit is being charged or partially discharged, thereby allowing voltage pulses to be applied to very many reaction spaces within a short time. Charging or partially discharging the first charge storing unit for a lower energy requirement is not a time-limiting factor, since the first charge storing unit is, for example, recharged or partially discharged during the longer-lasting discharge operation of one of the two second charge storing units.

In a further particularly advantageous development of the method according to the invention the method may comprise the following steps:

a) Applying at least one voltage pulse each to at least two reaction spaces by at least partially discharging two first charge storing units;
b) Applying at least one further voltage pulse each to the two reaction spaces from step a) by at least partially discharging two second charge storing units and simultaneously charging or partially discharging two further second charge storing units as well as the two first charge storing units at least partially discharged during step a);
c) Applying at least one voltage pulse respectively to the same reaction spaces or two further reaction spaces by at least partially discharging the two first charge storing units at least partially discharged during step a) and recharged or partially discharged during step b);
d) Applying at least one further voltage pulse to the two reaction spaces from step c) by at least partially discharging the two further second charge storing units charged or partially discharged during step b) and simultaneously charging or partially discharging the two second charge storing units at least partially discharged during step b) as well as the two first charge storing units at least partially discharged during step c).

At the start of the process according to the invention is started, preferably at least two first charge storing units are initially charged simultaneously or successively. At the end of the charging operations these two first charge storing units are then discharged, whereby a voltage pulse, preferably a short voltage pulse with a relatively high voltage amplitude, is applied, respectively, to at least two reaction spaces. One further voltage pulse, preferably a longer voltage pulse with a lesser voltage amplitude, is then applied, respectively, to these two reaction spaces after a short pause or without interruption, whereby these voltage pulses are generated by at least partially discharging the second charge storing units. At the same time as these second charge storing units are discharged, at least two further second charge storing units as well as the two first charge storing units are charged or partially discharged, so that the total process duration is not prolonged by the charge or discharge operations and so that the respective charge storing units are immediately available again when the next reaction space has to be treated. By subsequently discharging the two first charge storing units the same or two further reaction spaces can then be treated with a voltage pulse each. Thereafter the previously charged or partially discharged second charge storing units will again be at least partially discharged, whilst in parallel thereto in terms of time the previously discharged charge storing units are recharged or partially discharged. The previously described charge and discharge operations can be repeated as often as liked thus allowing a great many voltage pulses to be emitted in a relatively short period of time. In this way voltage pulses, in particular dual pulses, can be applied to a plurality of reaction spaces in a relatively short amount of time.

In an advantageous development of the invention all charge storing units can be charged ahead of step a) at the beginning of the process, thus allowing all charge storing units to be discharged as required. Alternatively the respective charge storing unit can be charged just prior to being discharged.

It is especially advantageous if at least two charge storing units, respectively, form a storage module, whereby always one of the charge storing units is at least partially discharged in the application or is ready to be discharged, whilst the other charge storing unit is charged or partially discharged so that the storage module holds the voltage required in total for the next voltage pulse in readiness, and thus can be at least partially discharged. The charge and discharge operations can be carried out synchronously or can be staggered in terms of time.

In an advantageous development of the method it is envisaged that the first charge storing units have a capacity of at least 10 µF, preferably at least 50 µF, in particular at least 100 µF, and/or are discharged at an initial voltage of between 10 and 1500 V, preferably between 20 and 1200 V, in particular between 50 and 1000 V, for a pulse duration of 2 µs to 40 ms, preferably 5 µs to 20 ms, in particular 10 µs to 10 ms.

In an advantageous development of the method it is further envisaged that the second charge storing units have a capacity of at least 100 µF, preferably at least 500 µF, in particular at least 1000 µF, and/or can be discharged at an initial voltage of between 10 and 240 V, preferably between 20 and 200 V, in particular between 50 and 150 V, for a pulse duration of 1 ms to 500 ms, preferably 2 ms to 350 ms, in particular 4 ms to 250 ms.

In particular in high throughput processes it is advantageously possible to repeat steps c) and d) or steps b) to e) at least 6, 8, 16, 24, 32, 48, 64, 96, 128, 192, 256, 384, 1536, 3456 or 6144 times.

It is possible to treat receptacles comprising several reaction spaces within short succession, preferably 6, 8, 16, 24, 32, 48, 64, 96, 128, 192, 256, 384, 1536, 3456 or 6144 times, with at least one voltage pulse, respectively.

It is especially advantageous if reaction spaces which are spaced far apart from each other are treated in succession, since in this way negative effects due to the development of heat caused by the voltage pulses can be better distributed.

Furthermore it is especially advantageous if discharging the charge storing units is controlled in such a way that at least two reaction spaces are treated in succession with voltage pulses of different voltages, where the voltage remaining in the respective charge storing unit after treating the first reaction space is as close as possible to the voltage of the subsequent voltage pulse to be emitted. Ideally the voltage remaining in the respective charge storing unit should be somewhat smaller than, somewhat larger than or approximately equal to the voltage of the subsequent voltage pulse to be emitted. In other words, a minimisation of the so-called "charging stroke" should preferably be attempted, i.e. one reaction space respectively should be chosen for the next voltage pulse, to which a voltage amplitude is applied which is closest to the voltage remaining in the charge storing unit, independently of whether the subsequent voltage is somewhat higher or somewhat lower. The important factor is that the charge or discharge operations necessary between the two voltage pulses should be minimised. Preferably with this embodiment pulsing should be carried out in ascending sequence, i.e. the voltage of the first voltage pulse should be lower than the voltage of the subsequent voltage pulse. In this way discharge operations between the voltage pulses can be avoided. By working sequentially through the voltage pulses the process duration can be additionally shortened in an advantageous way.

The invention also relates to a method for applying at least one electrical voltage pulse respectively to at least two reaction spaces by discharging at least one charge storing unit for storing electrical charges, where discharging the charge storing unit is controlled in such a way that voltage pulses of different voltages are applied to at least two reaction spaces in succession, where the voltage remaining in the charge storing unit following treatment of the first reaction space is as close as possible to the voltage of the subsequent voltage pulse to be emitted. Due to sequentially working through the voltage pulses as proposed by the invention the process duration can be distinctly reduced in an advantageous manner, since no time is needed for charge or discharge operations between two voltage pulses or since this time is at least distinctly reduced. Preferably the voltage remaining in the respective charge storing unit is somewhat smaller than, somewhat greater than or approximately equal to the voltage of the following voltage pulse to be emitted. That is, a minimisation of the so-called "charging stroke" should preferably be attempted, i.e. one reaction space respectively should be chosen for the next voltage pulse, to which a voltage amplitude is to be applied which is closest to the voltage remaining in the charge storing unit, independently of whether the subsequent voltage is somewhat higher or somewhat lower. The important factor is that the charge or discharge operations necessary between the two voltage pulses should be minimised. In an advantageous development of the invention pulsing should be carried out in ascending sequence, i.e. the voltage of the first voltage pulse should be lower than the voltage of the subsequent voltage pulse. In this way discharge operations between the voltage pulses can be avoided.

Since the charge storing unit, for example the feeding capacitor bank, emits energy during pulsing, the voltage in the charge storing unit is reduced. With regard to the next reaction space the charge storing unit must therefore be charged to match the voltage required for the next reaction space. If the voltages pulses within a contacting section are sorted, for example according to decreasing initial voltage, the charge as well as the discharge stroke can be minimised and the efficiency can thus be increased.

Furthermore the sequence in which the reaction spaces are worked within a contacting section, can be chosen for temperature-sensitive experiments in such a way that adjacent reaction spaces within a receptacle are pulsed at as large a time gap as possible in relation to each other in order to allow the temperature rise of a reaction space next to a just pulsed reaction space to subside as quickly as possible before this reaction space is treated with a voltage pulse.

Furthermore the object is met by a device, where at least two of the charge storing units form a common storage module, which can be discharged at any time so that these charge storing units form a unit which can always be discharged on demand after a first charge operation without an intermediate time-consuming charge or discharge operation having to be carried out.

The at least two charge storing units are preferably electrically coupled to a pulse generating unit, a switching unit and/or a distributing device for electrical voltage pulses via a common interface.

"Electrically coupled" in terms of the invention means that two components or elements of the electrical switching arrangement are electrically connected with each other either directly, i.e. without any elements switched in-between, or indirectly, i.e. with elements switched in between the components.

Furthermore at least one further charge storing unit may be provided, which is preferably electrically coupled, via a further interface, with the pulse-generating unit, the switching unit and/or the distributing device for electrical voltage pulses. In this way it is possible, to treat at least two reaction spaces simultaneously or to generate dual pulses for applying to at least one reaction space.

In these cases it is envisaged that the at least one further charge storing unit is electrically coupled to a power supply unit and that at least two charge storing units are electrically coupled to a common power supply unit. This embodiment is especially advantageous in cases where voltage pulses shall be generated which are composed of a short voltage pulse with relatively high voltage amplitude and a longer voltage pulse with lesser voltage amplitude. In this case the charge storing unit can generate a short voltage pulse whilst the storage module composed of two charge storing units provides a longer voltage pulse. With the device according to the invention therefore one of the two charge storing units of a storage module can always be discharged, while the other charge storing unit is charged, so that very many reaction spaces can be treated with voltage pulses within a short time. Charging the individual charge storing units is not a time-limiting factor, since this charge storing unit can be charged during the longer-lasting discharge operation of the storage module. Even given a case where the power supply unit (power pack) may not be strong enough and not fast enough, the time needed for the charge operation can be minimised due to the method according to the invention.

In an especially advantageous embodiment of the device according to the invention even four charge storing units may be provided, which in total form at least two storage modules.

It is of particular advantage if the storage module is electrically coupled, via a single or a common interface, with the pulse generating unit, the switching unit and/or the distributing device for electrical voltage pulses. Since, for example, four charge storing units may form two storage modules in total which can be respectively discharged at any time, two reaction spaces may always be treated simultaneously with one voltage pulse respectively due to the device according to the invention. Since no time is needed between two successive voltage pulses for charging a single capacitor, very many reaction spaces can therefore be treated with voltage pulses within a relatively short time using the device according to the invention. The device according to the invention is therefore particularly suitable for use in high throughput processes, where very many reaction spaces have to be treated with at least one voltage pulse each within a short time.

According to the invention at least two power supply units may be provided, whereby each power supply unit is electrically coupled with one storage module, respectively.

According to the invention, however, at least four power supply units and at least six charge storing units may also be provided. This embodiment of the device according to the invention can be advantageously used to great advantage, in particular in high throughput processes, where many reaction spaces have to be treated with dual voltage pulses within a short time. Using the device according to the invention two reaction spaces may always be treated simultaneously with voltage pulses. Thus, for example, two charge storing units may simultaneously emit a short voltage pulse with a relatively high voltage amplitude, which then, without interruption, changes into a longer voltage pulse with a lesser voltage amplitude. The longer voltage pulses may be provided by two storage modules, whereby always one of the two charge storing units of a storage module is discharged.

The charge storing units may be electrically coupled, via at least four interfaces, with the pulse generation unit, the switching unit and/or the distributing device.

At least two of the charge storing units may be electrically coupled with one power supply unit, respectively, and at least two storage modules may be provided which respectively comprise at least two charge storing units, whereby at least two of the storage modules are respectively electrically coupled with a common power supply unit.

In an especially advantageous embodiment of the device according to the invention it is envisaged that at least one charge storing unit is electrically coupled with a pulse generating unit, which in turn, preferably via a switching unit, is preferably electrically coupled with a distributing device for electrical voltage pulses.

In an advantageous embodiment of the invention it is envisaged that at least one of the charge storing units has a capacity of at least 10 µF, preferably at least 50 µF, in particular at least 100 µF.

Alternatively at least one of the charge storing units may have a capacity of at least 100 µF, preferably at least 500 µF, in particular at least 1000 µF.

The invention will now be explained in detail by way of example with reference to the figures.

FIGS. 1 to 6 each schematically show the time progression of particularly advantageous embodiments of the method according to the invention (R=reaction space).

FIGS. 7 to 12 each schematically show the construction of especially advantageous embodiments of the device according to the invention.

FIG. 1 schematically shows the time progression of a first especially advantageous embodiment of the method according to the invention. This embodiment is particularly suitable for applying at least one voltage pulse to at least one reaction space. This embodiment is particularly suitable for applying at least one voltage pulse to at least one reaction space. At the start of the process the charge storing unit designated CHV2A2 is initially charged. Subsequently this charge storing unit is discharged, so that at least one voltage pulse is applied to a first reaction space R1. The second charge storing unit CHV2A1 is charged or partially discharged in parallel with the first charge storing unit CHV2A2 being at least partially discharged. "Partially discharged" means that the charge storing unit is made ready to emit the next or subsequent voltage pulse, i.e. the voltage level in the charge storing unit is now adapted to match the voltage required for the next voltage pulse. This may be effected by either charging the charge storing unit up to the voltage required for the next voltage pulse or by partially discharging it down to the voltage specified for the next voltage pulse. In the second case the voltage level in the charge storing unit is adapted to match the new lower voltage level for the next reaction space in that it is partially discharged by means of a discharge device, for example via an electrical load, preferably by means of a discharge resistance. Consequently the second charge storing unit CHV2A1 is immediately available for the next discharge operation, if the first charge storing unit CHV2A2 was discharged. The next discharge operation can therefore begin without a pause immediately after the first discharge operation, so that no time is required or lost between two voltage pulses for charging or partially discharging a charge storing unit. Immediately after the first charge storing unit CHV2A2 has at least been partially discharged, discharging of the second charge storing unit CHV2A1, in this embodiment, therefore follows immediately without interruption. Due to this discharge operation, a further reaction space R2 is treated with a voltage pulse in the present embodiment. Alternatively the first reaction space R1 could also be treated with a further voltage pulse. Since simultaneously to discharging the second charge storing unit CHV2A1 the first charge storing unit CHV2A2 is recharged or partially discharged, the method according to the invention may be continued further without interruption, so that the same or further reaction spaces can be treated with voltage pulses. Due to simultaneously discharging and charging or partially discharging the charge storing units, one charge storing unit is always available for generating a voltage pulse so that the individual voltage pulses can be emitted directly one after the other. If a plurality of voltage pulses has to be emitted one after the other, be it in case one reaction space has to be treated with a number of several voltage pulses or several reaction spaces have to be treated with one voltage pulse each, the total process duration can be distinctly reduced therefore by using the method according to the invention. The method according to the invention is therefore particularly suitable for electroporation, electrofusion or similar methods in throughflow or high throughput processes. "Simultaneous" charging or discharging of the charge storing units in this context means that the charge and discharge operations run at least partially synchronously. The charge and discharge operations can therefore run either in parallel or can be staggered in terms of time. "Staggered in terms of time" means that an operation is still or already running whilst the other operation is already finished or has not yet started.

Figure 2:
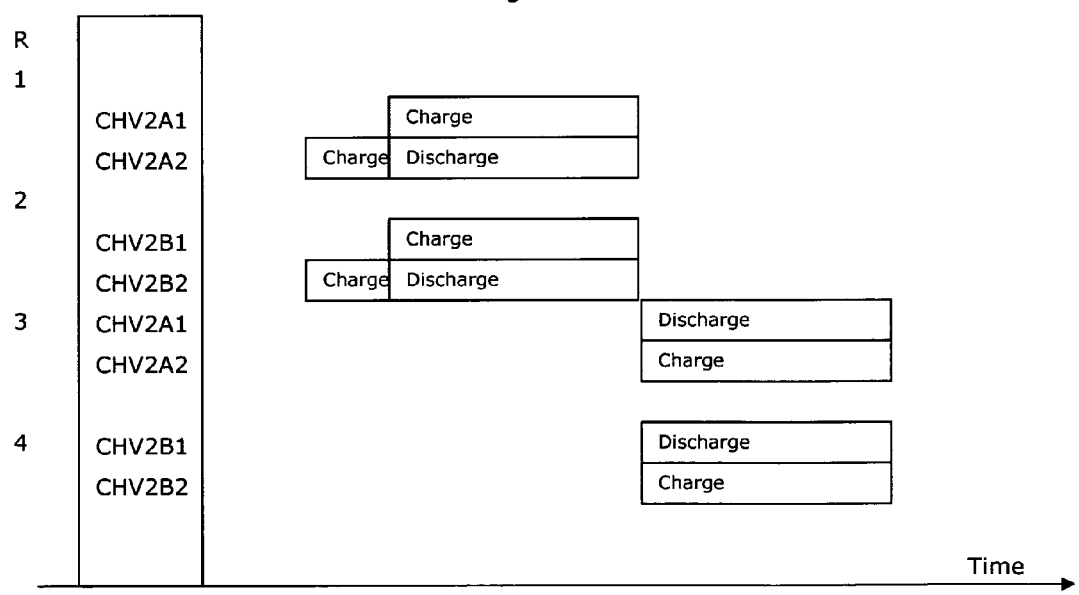

FIG. 2 schematically shows the time progression of a further embodiment of the method according to the invention. This embodiment is suitable, in particular, for treating at least two reaction spaces with at least one voltage pulse respectively. At the start of the process the charge storing units designated CHV2A2 and CHV2B2 are initially charged. These first charge storing units are subsequently at least partially discharged, so that at least two reaction spaces, here R1 and R2, are treated with one voltage pulse each. Simultaneously to the first two charge storing units being discharged, the two second charge storing units CHV2A1 and CHV2B1 are being charged. "Simultaneously" in terms of the invention means that the charge or discharge operations run at least partially synchronously, i.e. both operations may run synchronously or may be staggered in terms of time, whereby in the latter case one operation is still or already running, whilst the other operation has already terminated or not yet started. After completion of these charge and discharge operations the previously charged second charge storing units CHV2A1 and CHV2B1 are discharged and at the same time the previously discharged first charge storing units CHV2A2 and CHV2B2 are recharged or partially discharged. Thus the further reaction spaces R3 and R4 may be treated with a voltage pulse each, whilst the next voltage pulses are already being prepared. These steps may be repeated as often as liked. By simultaneously charging and discharging at least two charge storing units at least two reaction spaces can thus be simultaneously treated with a voltage pulse each, whereby the next two reaction spaces can directly subsequently be treated with voltage pulses without any time being lost for recharging or partially discharging the charge storing units. This is of particular advantage then when a plurality of reaction spaces must be treated with voltage pulses, since the total time to be spent on treating all reaction spaces with voltage pulses is considerably shortened.

FIG. 3 schematically shows the time progression of a special embodiment of the method according to the invention, which essentially corresponds to the method according to FIG. 2. The difference compared to the method according to FIG. 2 consists in that in this embodiment according FIG. 3 the same reaction spaces R1 and R2 are treated with several voltages pulses. Whilst in the embodiment of FIG. 2 further reaction spaces R3 and R4 are being electrically treated after the reaction spaces R1 and R2, the embodiment in FIG. 3 shows only reaction spaces R1 and R2 being treated with several voltage pulses following one another. It is, of course, also possible to combine the embodiments of FIG. 2 and FIG. 3 so that several reaction spaces can be treated one after the other with several voltage pulses respectively.

FIG. 4 schematically shows the time progression of an especially advantageous embodiment of the method according to the invention. This embodiment of the method according to the invention is particularly suitable for treating at least one reaction space with at least two electrical voltage pulses. At the start of the process the charge storing unit designated CHV1A is initially charged. This charge storing unit is then at least partially discharged, whereby the first reaction space R1 is treated with one voltage pulse. At some point in time during the charge or discharge operation of the charge storing unit CHV1A a second charge storing unit CHV2A2 is charged. This charge storing unit CHV2A2 is at least partially discharged immediately after discharging the first charge storing unit CHV1A, whereby herewith reaction space R1 is also treated with a corresponding voltage pulse. Reaction space R1 is thus treated in succession by two voltage pulses following one another, whereby these two voltage pulses, preferably without interruption, merge directly into one another. In a preferred embodiment of the present invention the first voltage pulse may be a short pulse with a relatively high voltage amplitude and the second voltage pulse may be a longer pulse with a lesser voltage amplitude. Alternatively the two voltage pulses may be emitted in succession with a more or less short pause so that a dual pulse with interruption is generated. Simultaneously with discharging the second charge storing unit CHV1A2 the further second charge storing unit CHV2A1 is charged. While discharging the second charge storing unit CHV2A2 the first charge storing unit CHV1A and a further second charge storing unit CHV2A1 are charged. Consequently, after completing discharging the second charge storing unit CHV1A, the two charge storing units CHV1A and CHV2A1 are immediately available again for the next discharge. Therefore the next reaction space R2 can be treated immediately thereafter without pause with a dual voltage pulse. This initially happens by at least partially discharging the first charge storing unit CHV1A and by at least partially discharging the further second charge storing unit CHV2A1 directly afterwards, without interruption. Due to the renewed at least partial discharging of the first charge storing unit CHV1A and the further second charge storing unit CHV2A1 the same reaction space R1 can, alternatively, be treated with a further voltage pulse. Simultaneously with at least partially discharging the further second charge storing unit CHV2A1 the first charge storing unit CHV1A and the second charge storing unit CHV2A2 are recharged or partially discharged, allowing the next dual voltage pulse to be emitted without delay. The above described charge and discharge operations may be repeated as often as liked, thereby allowing very many voltage pulses to be emitted in a relatively short time. The process duration is minimised, even when electrically treating many reaction spaces, since no time is lost between individual voltage pulses or the treatment of successive reaction spaces for charging or partially discharging the charge storing units.

FIG. 5 schematically shows the time progression of a further embodiment of the method according to the invention. This embodiment is suitable, in particular, for simultaneously treating at least two reaction spaces with at least two voltage pulses, respectively. At the start of the process at least four charge storing units are initially charged simultaneously or in succession. These four charge storing units are designated CHV1A, CHV2A2, CHV1B and CHV2B2 in the present embodiment. After completing the charge operation initially two first charge storing units CHV1A and CHV1B are at least partially discharged, whereby at least two first reaction spaces, here R1 and R2, are treated with one voltage pulse respectively. These two reaction spaces are treated, after a short pause or without interruption, with a further voltage pulse respectively, whereby these voltage pulses are generated by at least partially discharging the second charge storing units CHV2A2 and CHV2B2. Simultaneously with discharging these second charge storing units at least two further second charge storing units designated here CHV2A1 and CHV2B1 as well as the two first charge storing units CHV1A and CHV1B are charged or partially discharged. Due to subsequently at least partially discharging the two first charge storing units CHV1A and CHV1B the same reaction spaces (R1 and R2) or, as shown here, two further reaction spaces R3 and R4 can then be treated with one voltage pulse each. Subsequently (with or without interruption) the two previously charged second charge storing units CHV2A1 and CHV2B1 are then again discharged whilst in parallel thereto, in terms of time, the two previously discharged charge storing units CHV2A2 and CHV2B2 are recharged or partially discharged. The previously described charge and discharge operations may then be repeated as often as liked allowing very many voltage pulses to be emitted in a relatively short time. In this way a plurality of reaction spaces can be treated with voltage pulses, in particular with dual pulses, in a relatively short time.

FIG. 6 schematically shows the time progression of a special embodiment of the method according to the invention, which essentially corresponds to the embodiment of FIG. 5. The difference to the method according to the invention shown in FIG. 5 is that here the respectively first voltage pulses of a dual voltage pulse are generated not simultaneously (synchronously), but successively. This means that discharging the first charge storing units CHV1A and CHV1B takes place, respectively, in succession allowing reaction spaces R1 and R2 or R3 and R4 to be treated, not simultaneously, but one after the other with the first voltage pulses. The consequence of this is that the second voltage pulses of one dual voltage pulse are also emitted, not in parallel, but in a slightly staggered and overlapping fashion. With this special embodiment therefore, in contrast to the embodiment of FIG. 5, at least two reaction spaces are treated not simultaneously but in succession or in a slightly staggered fashion in terms of time. Due to this arrangement the total process duration may be, albeit, prolonged under certain circumstances, however this embodiment may be of advantage in cases, where undesirable side effects from the voltage pulses shall be avoided. Such an undesirable side effect may be an excessive heat development, for example.

Figure 7:
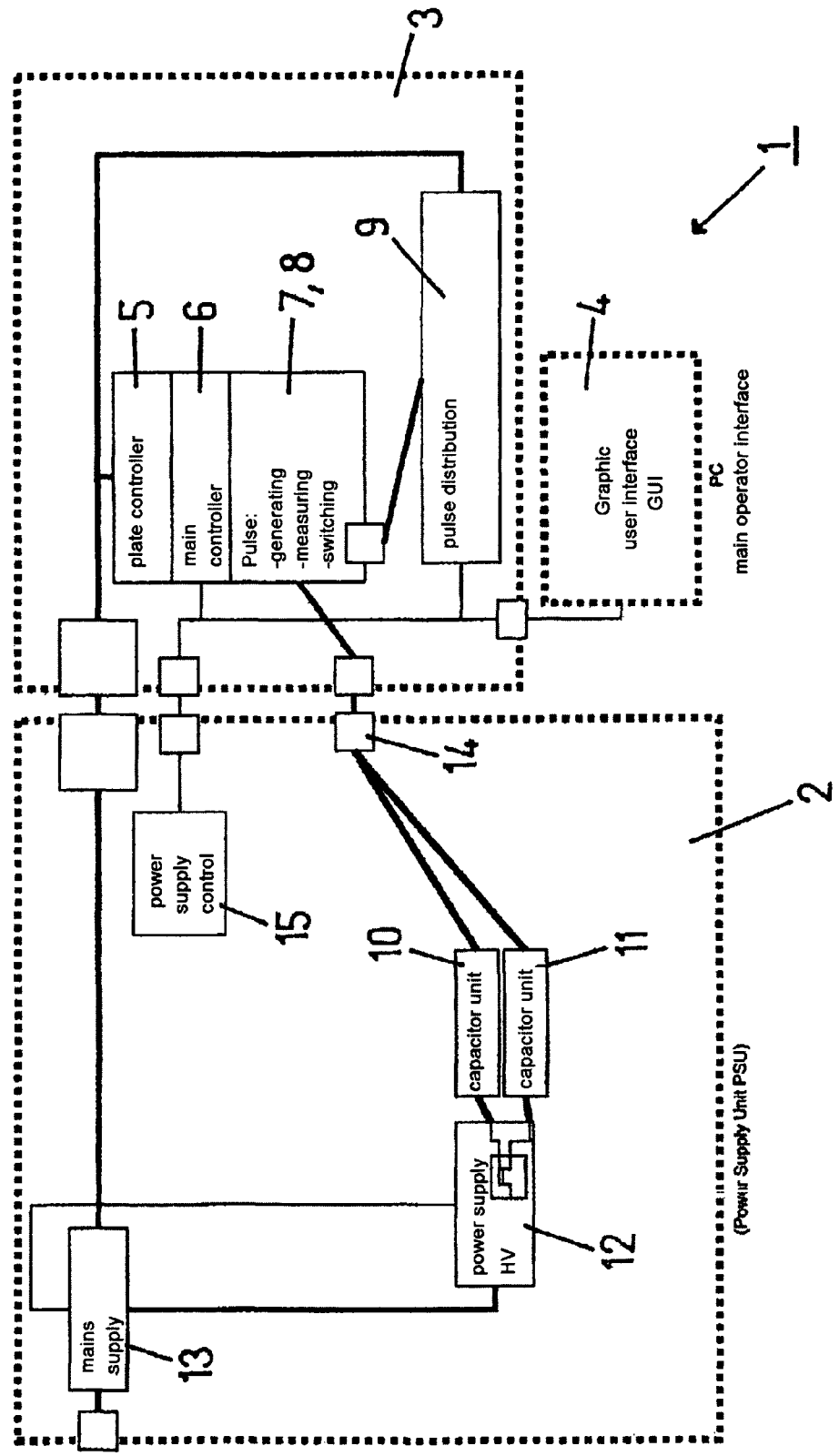

FIG. 7 schematically shows the construction of the device according to the invention for treating at least one reaction space with a voltage pulse. The device 1 according to the invention is essentially of modular construction and comprises at least one power supply module 2, one pulse distributing module 3 and one control module 4. The control module 4 comprises a control unit comprising a microprocessor and may, for example, be a conventional personal computer, preferably a laptop. The pulse distributing module 3 comprises a receptacle-controlling unit 5, which comprises the control for the receptacle, which comprises the reaction space or reaction spaces. The pulse distributing module 3 further comprises a central control unit 6 (main controller), which controls the distribution of the individual voltage pulses across the reaction space or reaction spaces. The pulse distributing module 3 also has a pulse generating unit 7 and a switching unit 8. The pulse generating unit 7 comprises elements which enable or control the transition of successive voltage pulses, such as a mixed switching circuit which includes analogue and digital elements. The switching unit 8 comprises the measuring circuits for the voltage pulses and the switches (for example IGBTs or MOSFETs) for discharging the charge storing units. The switching unit 8 is coupled with the distributing device 9 for electrical voltage pulses. The distributing device 9 comprises the switching devices (for example relays) for distributing the voltage pulses and the mechanical equipment for moving and positioning the receptacle or receptacles which comprise the reaction spaces.

The power supply module 2 in the embodiment of the device according to the invention shown in FIG. 7 essentially comprises two charge storing units 10, 11, which can be charged from a common power supply unit 12. The power supply unit 12 is controlled by means of the power supply control 15. Further, at least one discharge device not shown here is provided, via which the charge storing units 10, 11 can be partially discharged. The discharge device may be a discharge resistance, for example. In the present embodiment the power supply module 2 further comprises a central mains supply unit 13 which ensures the voltage supply in the entire device 1. The two charge storing units 10, 11 form a storage module which is connected with the pulse distributing unit 3 via a common interface 14. The storage module, i.e. the charge storing units 10 and 11, are thus electrically coupled, in the present embodiment, with the distributing device 9 via the pulse generating unit 7 and the switching unit 8. Due to the fact that the two charge storing units 10, 11 form a storage module, in which one of the two charge storing units 10, 11 is always charged by the power supply unit 12, whilst the other charge storing unit 10, 11 can be charged or partially discharged, the storage module is altogether available at any time for holding a voltage pulse ready. This kind of construction allows very many voltage pulses to be emitted within a relatively short time, since in comparison to a single charge store no time is lost for recharging or partially discharging the charge store. The charge storing units 10, 11 may be individual capacitors or whole banks of capacitors, respectively, which consist of several capacitors switched in parallel and/or in series.

The generation of high voltages, in particular of more than 1000 V, is connected with a certain expenditure on the side of the electronics, since especially voltage-proof elements must be used here and certain distances between the live printed high-voltage lines on the board must be adhered to, in order to ensure a high dielectric strength of the electronics. Secondly the manufacture of high-voltage power packs which are able to provide adequate charge and thus energy amounts for the high voltages needed in electroporation is very cumbersome and expensive. On the other hand, however, it may be of advantage or even necessary for efficient electroporation or through a special construction of the electroporation device (for example large distances between the electrodes), to generate such high voltages (in particular >1000 V). Therefore there is a requirement to reduce these costs for the charge (and discharge) device of an energy store (for example a capacitor or capacitor battery) to a minimum. In order to generate high voltages on the pulse side (emission of a pulse by the energy store to a reaction space), but to avoid these voltages on the charging side (charging the energy store from a power pack which draws its energy from the current grid), one can use several independently interconnectable capacitors (or other storage units) in such a way as to interconnect them all in parallel by means of a power pack, for example when charging them up to a voltage U, and accept an n-times increased charging current compared to a series interconnection and thus an n-times increased charge amount n*Q. If these charging units are interconnected in series upon completion of the charging operation, the voltage $n*U_{Lade}$ ($U_{Lade}$=charging voltage) is obtained, which can be utilised during pulse discharging across the reaction space. The electronics on the charging side and the individual capacitors themselves only need to be designed for a relatively low voltage $U_{Lade}$, for example 1000 V, which means a distinct saving on cost and also space (resistance against spark-over, for example, between printed lines on printed circuit boards means larger distances or, where possible and sensible, additional insulation measures). Only the secondary discharging side has to be correspondingly voltage-stable for $n*U_{Lade}$.

Figure 8:
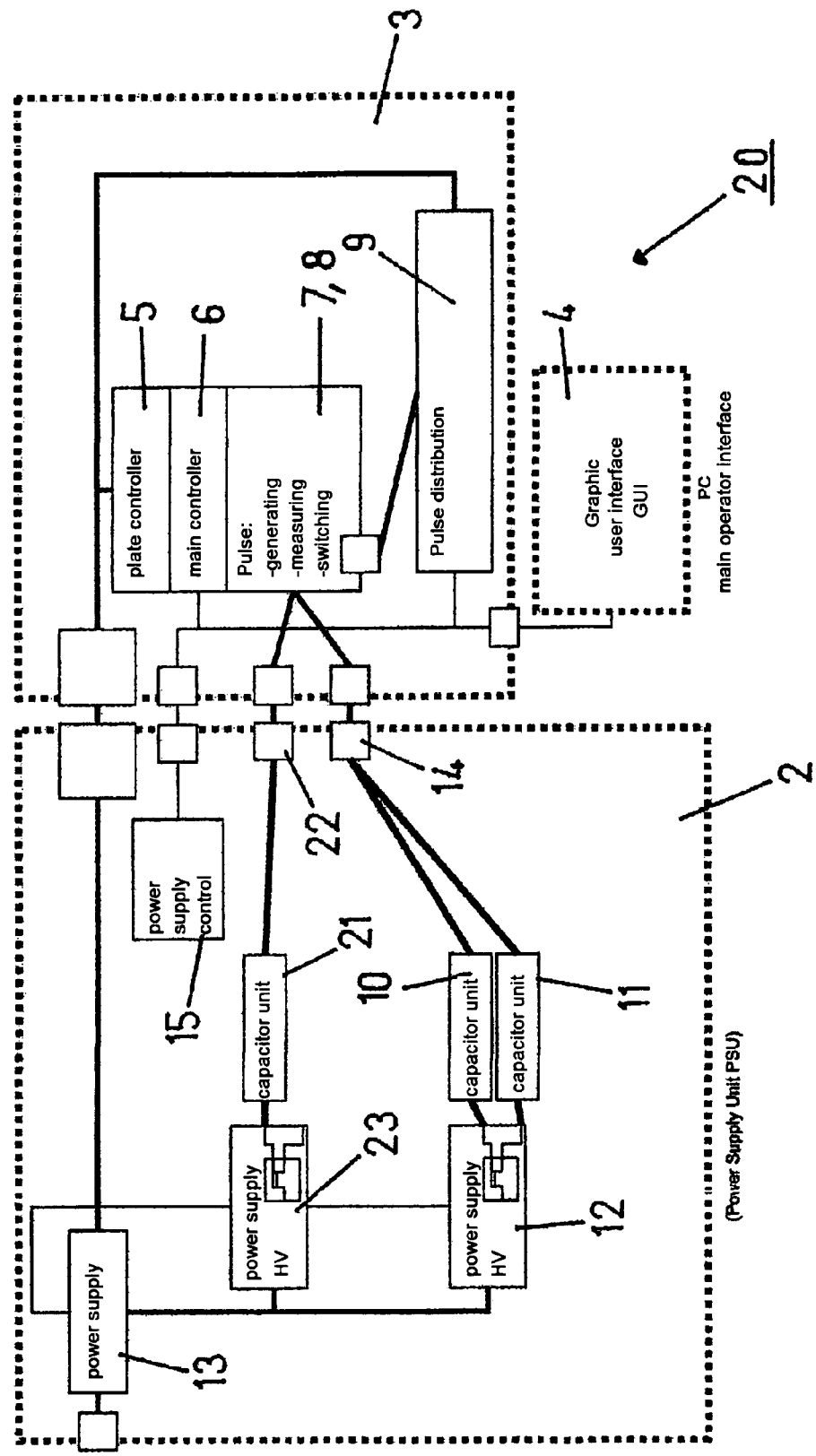

FIG. 8 schematically shows the construction of a further embodiment of the device according to the invention. The device 20 is suitable for treating at least one reaction space with at least two voltage pulses. The device 20 corresponds to the device 1 of FIG. 7 as regards the modular construction and the essential components. For this reason identical components in FIG. 8 are marked with the same reference numbers as in FIG. 7. The device 20 according to the invention of FIG. 8 is different from the device 1 in FIG. 7 in that a further charge storing unit 21 is provided, which is coupled with the distributing device 9 via a further interface 22. The charge storing unit 21 is supplied from a further power supply unit 23 and enables treating the reaction space or reaction spaces with dual voltages in rapid succession or without interruption and which merge into one another. This embodiment is of advantage in particular, where voltage pulses are to be generated, which are composed of a short voltage pulse, preferably with a relatively high voltage amplitude, and a longer voltage pulse, preferably with a lesser voltage amplitude. In this case the charge storing unit 21 can generate a short voltage pulse, whilst the storage module composed of charge storing units 10 and 11 provides a longer voltage pulse. Combining or merging of the individual voltage pulses to form a dual voltage pulse takes place in the pulse generating unit 7. Where several reaction spaces shall be treated in succession within a relative short time with such dual voltage pulses, for example when using multiwell plates in high-throughput processes, the distances between the treatment of individual reaction spaces would be relatively long when using a single capacitor for the longer voltage pulse, since the capacitor would first have to be recharged after discharging. With the device 20 according to the invention, however, one of the two charge storing units 10, 11 can always be partially discharged, whilst the other charge storing unit 10, 11 is charged or discharged, thus allowing very many reaction spaces to be treated within a short time with voltage pulses. Charging or partially discharging the charge storing unit 21 is not a time-limiting factor, since the charge storing unit 21 can be charged or partially discharged during the longer-lasting discharge operation of the storage module.

Figure 9:
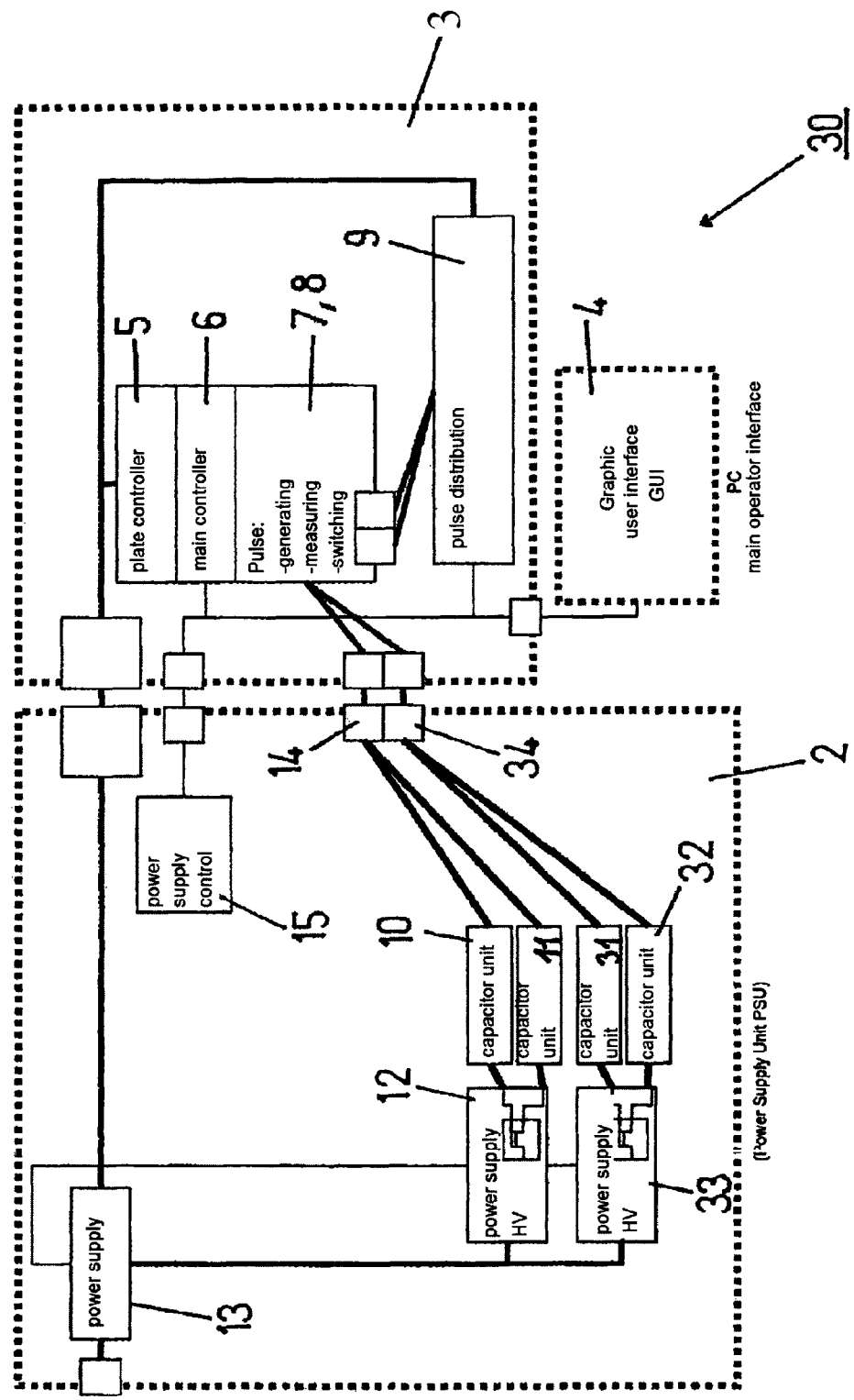

FIG. 9 schematically shows the construction of a further embodiment of the device according to the invention, whereby this embodiment is particularly suitable for carrying out the method according to the invention treating at least two reaction spaces with one electrical voltage pulse, respectively. The device 30 according to the invention also corresponds to the device 1 of FIG. 7 with regard to its modular construction and essential components, whereby identical components are marked again with the same reference numbers, respectively. The device 30 according to the invention is different from the device 1 of FIG. 7 in that the power supply module 2 comprises two additional charge storing units 31, 32 and an additional power supply unit 33. The charge storing units 31, 32 form a storage module, which can be charged from the common power supply unit 33 and is electrically coupled via the common interface 34 and the pulse generating unit 7 or the switching unit 8 with the distributing device 9. Since the charge storing units 10, 11, 31, 32 in total form two storage modules which can be discharged respectively at any time, two reaction spaces can always be simultaneously treated with a voltage pulse respectively by the device 30 according to the invention. Since, as described above, no time is required between two successively voltage pulses for charging a single capacitor, very many reaction spaces can be treated with voltage pulses in a relative short time by means of the device 30 according to the invention. The device 30 according to the invention is therefore suitable, in particular, for use in high throughput processes, where a great many reaction spaces must be treated within a short time with one voltage pulse respectively.

Figure 10:
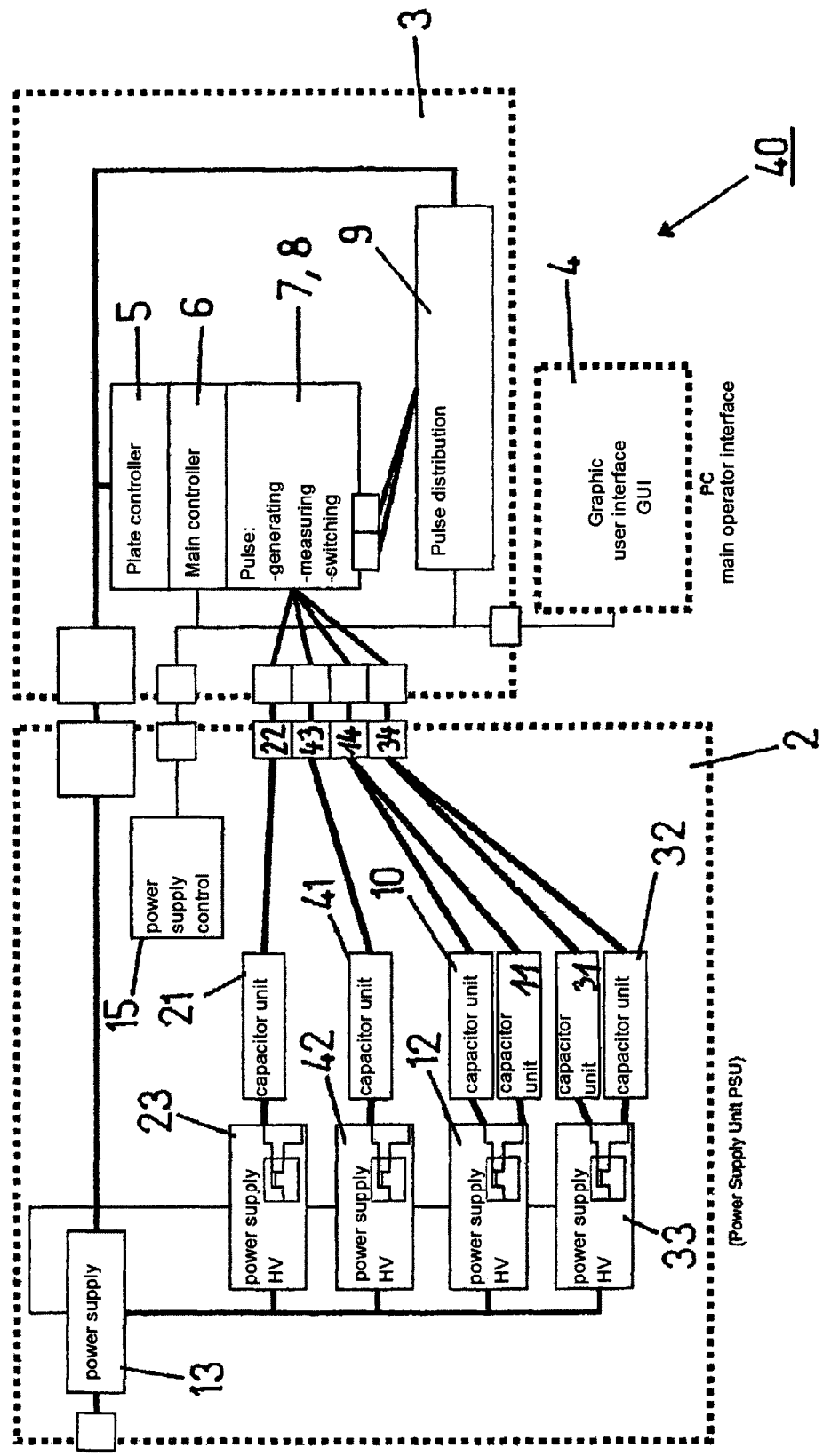

FIG. 10 schematically shows a further embodiment of the device according to the invention, which in principle is composed of components of the device 20 according to the invention as shown in FIG. 8 and of the device 30 according to the invention as shown in FIG. 9. Here again, therefore, identical components are marked with the same reference numbers. The device 40 according to the invention additionally comprises a further charge storing unit 41 within the power supply module 2, which charge storing unit can be charged from its own power supply unit 42 and is electrically coupled with the distributing device 9 via it own interface 43. The device 40 according to the invention thus has, in total, 6 charge storing units 10, 11, 21, 31, 32, 41 within the power supply module 2 which, in total, are coupled with the distributing device 9 via four interfaces 14, 22, 34, 43. Two charge storing units 10 and 11 or 31 and 32, respectively, form two storage modules in total, which, as described above, can be discharged at any time. The charge storing units 10, 11, 21, 31, 32, 41 are charged via four power supply units 12, 23, 33, 42 in total, whereby each storage module is associated with a power supply unit 12, 33 respectively. Alternatively it would be possible to charge the charge storing units 10, 11, 21, 31, 32, 41 from a voltage supply device, for example directly from one of the power supply units 12, 23, 33 or 42. The device 40 according to the invention can be used with particular advantage in high throughput processes, where many reaction spaces have to be treated within a short time with dual voltage pulses. Two reaction spaces can always be treated simultaneously with voltage pulses by means of the device 40 according to the invention. Thus, for example, the charge storing units 21 and 41 can emit a short voltage pulse with a relatively high voltage amplitude respectively, which then changes, without interruption, to become a longer voltage pulse with lesser voltage amplitude.

The longer voltage pulses may be made available by the two storage modules, whereby always one of two charge storing units 10, 11 or 31, 32 of a storage module can be discharged. In this embodiment the dual voltage pulses are assembled in the pulse generating unit 7.

Figure 11:
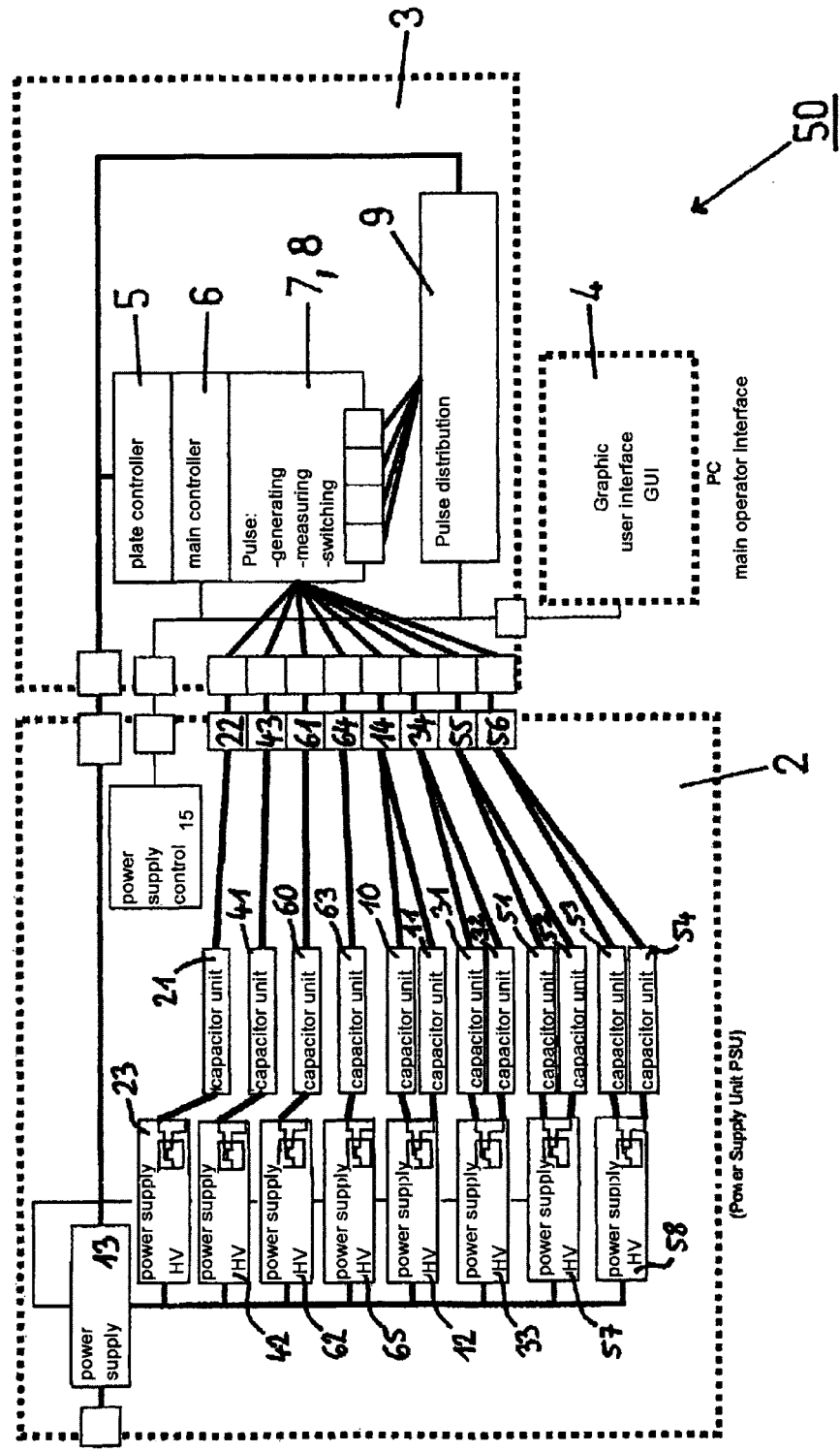

FIG. 11 shows a further special embodiment of the device according to the invention, which in its construction corresponds in principle to the device 40 of FIG. 10. The device 50 according to the invention of FIG. 11 is different from the device 40 of FIG. 10 in that the components of the power supply module 2 are duplicated. Therefore, using the device 50 according to the invention four reaction spaces can be treated simultaneously with voltage pulses. The device 50 according to the invention additionally comprises two further storage modules which are formed by the charge storing units 51 and 52 or 53 and 54, whereby the two additional storage modules are electrically coupled with the distributing device 9 via an interface 55 or 56, respectively. Each additional storage module is charged via its own power supply unit 57 or 58. In order to enable four reaction spaces to be treated simultaneously with voltage pulses two further charge storing units 60 and 63 are provided, which are coupled with the distributing device 9 via a separate interface 61 or 64, respectively, and can be charge via their own power supply unit 62 or 65, respectively. By means of the device 50 according to the invention therefore, the time for treating the same number of reaction spaces can be distinctly reduced or the number of reaction spaces to be treated can be distinctly increased compared to the device 40 according to the invention of FIG. 10. The number of charge storing units or storage modules can, of course, be further increased in order to be able to treat even more reaction spaces simultaneously with voltage pulses.

Figure 12:
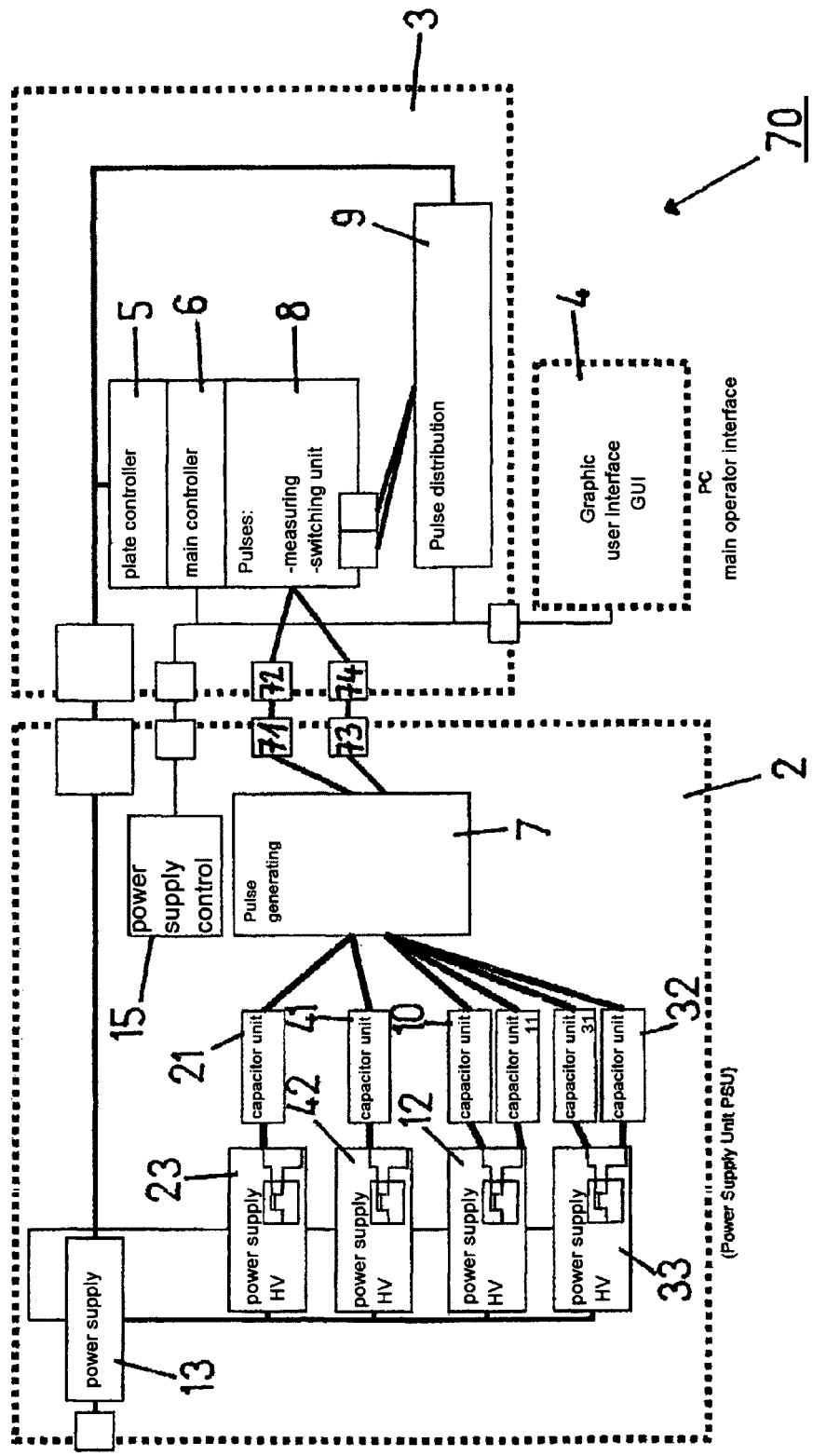

FIG. 12 schematically shows the construction of a special embodiment of the device according to the invention, which essentially corresponds to the device 40 according to the invention of FIG. 10. Here again identical components have been marked with the same reference numbers. The device 70 of FIG. 12 differs from the embodiment of FIG. 10 in that here the pulse generating unit 7 is arranged inside the power supply module 2. Thus the pulse generating unit 7 in this embodiment is not arranged as a unit with the switching unit 8 inside the pulse distributing module 3. The charge storing units 10, 11, 21, 31, 32, 41 in this embodiment are therefore coupled directly with the pulse generating unit 7. The advantage of this is that here the dual voltage pulse with which the reaction spaces are treated can be assembled already in the power supply module 2 before the voltage pulse is passed on to the distributing device 9 via the switching unit 8. The dual voltage pulse is generated inside the pulse generating unit 7 from the first voltage pulse made available by the charge storing unit 21 or 41 and the second voltage pulse made available by the charge storing units 10 or 11 and 31 or 32, respectively. The complete dual voltage pulse is then passed on to the switching unit 8 via the interfaces 71 and 72 or 73 and 74. The pulse generating unit 7 may, for example, comprise a mixed switching circuit which includes analogue and digital elements and via which the first and second voltage pulse can be combined to form a dual voltage pulse. Especially advantageous in this embodiment is the fact that the high voltage cables to be arranged between the device units are reduced. Since these cables and the associated connection techniques are expensive, the complexity as a whole can be reduced and the reliability, in particular in high throughput processes, can be increased.

LIST OF REFERENCE SYMBOLS

1 Device
2 Power supply module
3 Pulse distributing module
4 Control module
5 Receptacle controlling unit
6 Control unit (Main Controller)
7 Pulse generating unit
8 Switching unit
9 Distributing device
10 Charge storing unit
11 Charge storing unit
12 Power supply unit
13 Power pack
14 Interface
15 Power Pack control
20 Device
21 Charge storing unit
22 Interface
23 Power supply unit
30 Device
31 Charge storing unit
32 Charge storing unit
33 Power supply unit
34 Interface
40 Device 41 Charge storing unit
42 Power supply unit
43 Interface
50 Device
51 Charge storing unit
52 Charge storing unit
53 Charge storing unit
54 Charge storing unit
55 Interface
56 Interface
57 Power supply unit
58 Power supply unit
60 Charge storing unit
61 Interface
62 Power supply unit
63 Charge storing unit
64 Interface
65 Power supply unit
70 Device
71 Interface
72 Interface
73 Interface
74 Interface

The invention claimed is:

1. A method for applying at least one electrical voltage pulse to at least one reaction space by at least partially discharging at least one charge storing unit for storing electrical charges, said method comprises:
   a) Providing more than two charge storing units, two or more of said charge storing units being part of a storage module, wherein each of the charge storing units is at least partially discharged to said at least one reaction space, and wherein each storage module is configured to hold a voltage required for a voltage pulse ready at any time,
   b) Applying at least one voltage pulse to at least one reaction space by at least partially discharging a first charge storing unit of said module and simultaneously charging or partially discharging a second charge storing unit of said module;
   c) Directly subsequent to b) without a time interruption, applying at least one further voltage pulse to the same reaction space or a further reaction space by at least partially discharging the second charge storing unit of said module and simultaneously charging or partially discharging the first charge storing unit of said module discharged during b).

2. Method according to claim 1, comprising:
   a) wherein said at least one voltage pulse is applied to at least two reaction spaces by at least partially discharging two first charge storing units and simultaneously charging or partially discharging two second charge storing units; and
   b) wherein said at least one further voltage pulse is applied to the same reaction spaces or to a further two reaction spaces by at least partially discharging the two second charge storing units and simultaneously charging or partially discharging the two first charge storing units at least partially discharged during a).

3. A method for applying at least one electrical voltage pulse to at least one reaction space by at least partially discharging at least one charge storing unit for storing electrical charges, said method comprising:
   a) Providing more than two charge storing units, one or more of said charge storing units being single units and two or more of said charge storing units being part of a storage module, wherein each of the charge storing units is at least partially discharged to said at least one reaction space, and wherein each storage module is configured to hold a voltage required for a voltage pulse ready at any time;
   b) Applying at least one voltage pulse to at least one reaction space by at least partially discharging a first charge storing unit, the first charge storing unit being a single unit;
   c) Applying at least one further voltage pulse to the reaction space by at least partially discharging a second charge storing unit and simultaneously charging or partially discharging a further second charge storing unit as well as the first charge storing unit discharged during b), wherein the second charge storing units are part of a storage module;
   d) Applying at least one voltage pulse to another or the same reaction space by at least partially discharging the first charge storing unit at least partially discharged during b) and recharged or partially discharged during c);
   e) Applying at least one further voltage pulse to the reaction space from d) by at least partially discharging the further second charge storing unit charged or partially discharged during c) and simultaneously charging or partially discharging the second charge storing unit at least partially discharged during c) as well as the first charge storing unit at least partially discharged during d).

4. A method for applying at least one electrical voltage pulse to at least one reaction space by at least partially discharging at least one charge storing unit for storing electrical charges, said method comprising:
   a) Providing more than five charge storing units, two or more of said charge storing units being single units and four or more of said charge storing units being part of two or more storage modules, wherein each of the charge storing units is at least partially discharged to said at least one reaction space, and wherein each storage module is configured to hold a voltage required for a voltage pulse ready at any time;
   b) Applying at least one voltage pulse each to at least two reaction spaces by at least partially discharging two first charge storing units, each first charge storing unit being a single unit;
   c) Applying at least one further voltage pulse each to the two reaction space from b) by at least partially discharging two second charge storing units and simultaneously charging or partially discharging two further second charge storing units as well as the two first charge storing units at least partially discharged during b), wherein each second charge storing unit is part of a storage module and each storage module comprises two second charge storing units;
   d) Applying at least one voltage pulse respectively to the same reaction spaces or two further reaction spaces by at least partially discharging the two first charge storing units at least partially discharged during b) and recharged or partially discharged during c);
   e) Applying at least one further voltage pulse to the two reaction spaces from step d) by at least partially discharging the two further second charge storing units charged or partially discharged during c) and simultaneously charging or partially discharging the two second charge storing units at least partially discharged during c) as well as the two first charge storing units at least partially discharged during d).

* * * * *